(12) United States Patent
Shemer et al.

(10) Patent No.: US 7,187,970 B2
(45) Date of Patent: *Mar. 6, 2007

(54) EXCITABLE TISSUE CONTROL SIGNAL DELIVERY TO THE RIGHT VENTRICULAR SEPTUM

(75) Inventors: Itsik Shemer, Zichron Yaakov (IL); Yuval Mika, Shmurat Zichron Yaakov (IL)

(73) Assignee: Impulse Dynamics (Israel) Ltd, Tirat Hacarmel (IL)

( * ) Notice: Subject to any disclaimer, the term of this patent is extended or adjusted under 35 U.S.C. 154(b) by 462 days.

This patent is subject to a terminal disclaimer.

(21) Appl. No.: 10/672,385

(22) Filed: Sep. 26, 2003

(65) Prior Publication Data

US 2004/0138710 A1    Jul. 15, 2004

Related U.S. Application Data

(63) Continuation-in-part of application No. 10/188,726, filed on Jul. 2, 2002, and a continuation of application No. 09/848,535, filed on May 3, 2001, now abandoned, and a continuation-in-part of application No. 10/039,845, filed on Oct. 23, 2001, which is a continuation of application No. 09/563,544, filed on May 1, 2000, now Pat. No. 6,363,279, which is a continuation of application No. 09/254,903, filed on Mar. 12, 1999, now Pat. No. 6,415,178, which is a continuation of application No. 09/101,723, filed on Aug. 13, 1998, now Pat. No. 6,317,631, application No. 08/595,365, filed on Feb. 1, 1996, now Pat. No. 5,738,096.

(60) Provisional application No. 60/202,382, filed on May 4, 2000, provisional application No. 60/009,769, filed on Jan. 11, 1996, provisional application No. 60/011,117, filed on Feb. 5, 1996, provisional application No. 60/026,392, filed on Sep. 16, 1996, provisional application No. 60/026,392, filed on Sep. 16, 1996.

(30) Foreign Application Priority Data

Sep. 17, 1996   (IL) .................................... 119261

(51) Int. Cl.
  *A61N 1/00*   (2006.01)
  *A61N 1/362*  (2006.01)
(52) U.S. Cl. .............................................. 607/2; 607/9
(58) Field of Classification Search ..................... None
  See application file for complete search history.

(56) References Cited

U.S. PATENT DOCUMENTS 4,237,895 A    12/1980  Johnson (Continued)

FOREIGN PATENT DOCUMENTS

EP            148 687         7/1985

(Continued)

OTHER PUBLICATIONS

Hoffman, B.F. et al., "Effects of Postextrasystolic Potentiation on Normal and Failing Hearts", Bulletin of New York Academy of Medicine, 41 in 1965, pp. 498-534.

(Continued)

*Primary Examiner*—Robert E. Pezzuto
*Assistant Examiner*—Kristen Mullen
(74) *Attorney, Agent, or Firm*—Wolf, Block, Schorr & Solis-Cohen LLP; William H. Dippert

(57) ABSTRACT

Apparatus for applying a signal to a heart of a human subject is provided. The apparatus includes a set of one or more electrodes, adapted to be coupled to the right ventricular septum of the heart. A control unit of the apparatus is adapted to drive the electrode set to apply an Excitable-Tissue Control (ETC) signal to the septum. Preferably, the control unit is adapted to configure the signal to be capable of modifying contractility of a portion of the heart.

32 Claims, 7 Drawing Sheets

U.S. PATENT DOCUMENTS

| | | | |
|---|---|---|---|
| 4,312,354 A | | 1/1982 | Walters |
| 4,384,585 A | | 5/1983 | Zipes |
| 4,440,172 A | | 4/1984 | Langer |
| 4,543,956 A | * | 10/1985 | Herscovici .................. 607/13 |
| 4,554,922 A | | 11/1985 | Prystowsky et al. |
| 4,559,947 A | | 12/1985 | Renger et al. |
| 4,674,508 A | | 6/1987 | DeCote |
| 4,726,379 A | | 2/1988 | Altman et al. |
| 4,971,058 A | | 11/1990 | Pless et al. |
| 4,979,507 A | | 12/1990 | Heinz et al. |
| 4,998,531 A | | 3/1991 | Bocchi et al. |
| 5,044,375 A | | 9/1991 | Bach, Jr. et al. |
| 5,083,564 A | | 1/1992 | Scherlag |
| 5,154,501 A | | 10/1992 | Svenson et al. |
| 5,172,699 A | | 12/1992 | Svenson et al. |
| 5,184,620 A | | 2/1993 | Cudahy et al. |
| 5,205,284 A | | 4/1993 | Freeman |
| 5,213,098 A | | 5/1993 | Bennett et al. |
| 5,267,560 A | * | 12/1993 | Cohen ........................ 607/25 |
| 5,281,219 A | | 1/1994 | Kallok |
| 5,320,642 A | | 6/1994 | Scherlag |
| 5,366,486 A | | 11/1994 | Zipes et al. |
| 5,391,199 A | | 2/1995 | Ben-Haim |
| 5,417,717 A | | 5/1995 | Salo et al. |
| 5,443,489 A | | 8/1995 | Ben-Haim |
| 5,531,764 A | | 7/1996 | Adams et al. |
| 5,549,646 A | | 8/1996 | Katz et al. |
| 5,662,687 A | | 9/1997 | Hedberg et al. |
| 5,738,096 A | | 4/1998 | Ben-Haim |
| 5,749,906 A | | 5/1998 | Kieval et al. |
| 5,792,208 A | | 8/1998 | Gray |
| 5,800,464 A | | 9/1998 | Kieval |
| 5,814,079 A | | 9/1998 | Kieval |
| 5,871,506 A | | 2/1999 | Mower |
| 6,330,476 B1 | * | 12/2001 | Ben-Haim et al. ............. 607/9 |

FOREIGN PATENT DOCUMENTS

| | | |
|---|---|---|
| EP | 727 241 | 8/1996 |
| JP | 436 5493 | 12/1992 |
| JP | 712 6600 | 5/1995 |
| WO | WO 97/25098 | 7/1997 |
| WO | WO 98/10828 | 3/1998 |
| WO | WO 98/10830 | 3/1998 |
| WO | WO 98/10831 | 3/1998 |
| WO | WO 98/10832 | 3/1998 |
| WO | WO 99/09971 | 3/1999 |

OTHER PUBLICATIONS

King A. et al., The Inotropic Action of Paired Pulse Stimulation in The Normal and Failing Heart: An Experimental Study, Cardiovascular Research, vol. 2, Apr. 1968, pp. 122-129.

Dillon, SM., "Optical Recordings In the Rabbit Heart Show that Defibillation Strength Shocks Prolong the Duration of Depolarization and the Refractory Period" In Circ Res., 69 (3), Sep. 1991, pp. 842-856.

Sweeny RS, et al., Ventricular Refractory Period Extension Caused by Defibrilation Shocks, Circulation, Sep. 1990, vol. 62, No. 3, pp. 965-972.

Gill RJ, et al., abstract of "Refractory Period Extension During Ventricular Pacing at Fibrillatory Pacing Rates", Pacing Clin. Electrophysiol, Mar. 1997, vol. 20, No. 3, pp. 647-653.

Sweeny RJ, et al., abtract of "Refractory Interval After Transcardiac Shocks During Ventricular Fibrillation", Circulation, Dec. 1996, vol. 94, No. 11, pp. 2947-2952.

Sweeney RJ, et al., abstract of "Countershock Strength-Duration Relationship for Myocardial Refractory Period Extension", Acad Emerg. Med., Jan. 1995, vol. 2, No. 1, pp. 57-62.

Dillon, SM, abstract of "Synchronized Repolarization After Defibrillation Shocks. A Possible Component of the Defibrillation Process Demonstration By Optical Recordings In Rabbit Heart", Circulation, May 1992, vol. 85, No. 5, pp. 1865-1878.

Saksena et al., "Dual-Site Atrial Pacing in Atrial Fibrilation", JACC, vol. 28, No. 3, Sep. 1996, pp. 687-694.

Thakor et al. "Effect of Varying Pacing Waveform Shapes on Propagation and Hemodynamics In the Rabbit Heart", The American Journal Of Cardiology 79(6A), pp. 36-43. 1997.

Franz, M.R., "Method and Theory of Monophasic Action Potential Recording", Prog. Cardiovasc Dis 33(6), May-Jun. 1991, pp. 347-368.

Franz, M.R., "Bridging The Gap Between Basic And Clinical Electrophysiology: What Can Be Learned From Monophasic Action Potential Recordings?", J. Cardiovasc Electrophysiol 5(8), Aug. 1994, pp. 699-710.

Bargheer K., et al., "Prolongation Of Monophasic Action Potential Duration And The Refractory Period In The Human Heart By Tedisamil, A New Potassium-Blocking Agent", J. Eur Heart 15(10), Oct. 1994, pp. 1409-1414.

Franz, M.R., "Progress In Cardiovascular Diseases: Monophasic Action Potential Symposium, I. Introduction", Prog. Cardiovasc Dis 33(6), May-Jun. 1991, pp. 345-346.

McVeigh E.R., et al., "Noninvasive Measurement of Transmural Gradients In Myocardial Strain with MR Imaging", Radiology 180(3), Sep. 1991, pp. 677, 679-684.

Bers, D.M., Excitation-Contraction Coupling and Cardiac Contractile Force. 1991.

Zipes, D., et al., Cardiac Electrophysiology From Cell To Bedside, 1990, W.B. Saunders Co., Philadelphia 1990.

Josephson, M.E., Clinical Cardiac Electrophysiology: Techniques And Interpretations, 2nd Edition, Lea & Febiger, Philadelphia, 1991.

Wessale, J.L. et al. , "Stroke Volume and Three Phase Cardiac Output Rate Relationship With Ventricular Pacing", PACE 13, May 1990. pp. 673-680.

Wirtzfeld, A., et al., "Physiological Pacing: Present Status And Future Deelopments", PACE 10 Jan.- Feb. 1987, Part 1, pp. 41-57.

Talit, U., et al. "The Effect of External Cardiac Pacing on Stroke Volume". PACE 13, May 1990, pp. 598-602.

Webster, John G., ed., Design of Cardiac Pacemakers, IEEE Press, Piscataway, NJ 1995.

Fain, E.S., et al., "Improved Internal Defibrillation Efficacy With a Biphasic Waveform", American Heart Journal, 117(2), Feb. 1989, pp. 358-364.

Fromer, et al., "Ultrarapid Subthreshold Stimulation For Termination Of Atrioventricular Node Reentrant Tachycardia", Journal of the American College of Cardiology 20 (Oct. 1992), pp. 879-883.

Knisley, et al. "Prolongation and Shortening of Action Potentials by Electrical Shocks in Frog Ventricular Muscle", American Journal of Physiology 6 (Heart Circ. Physiol. 35. 1994) pp. H2348-H2358.

Antonl, H., et al., "Polarization Effects of Sinusoidal 50 Hz Alternating Current On Membrane Potential of Mammalian Cardiac Fibres",Pflugers Arch. 314, pp. 274-291, 1969.

"http://picuBOOKnet", Apr. 2000,pp. 1-10.

Cooper, W., "Postextrasystolic Potentiation: Do We REally Know What It Means And How To Use It?", Circualation, vol. 88, No. 6, Dec. 1993, pp. 2962-2971.

Foster, A.H., et al., "Acute Hemodyamic Effects of Atrio-Biventricular Pacing In Humans", 1996, The Society of Thoracic Surgeons vol. 59, pp. 294-299.

Cezeau, S., et al., "Multisite Pacing For End-Stage Heart Failure: Early Experience", Pacing and Clincial Electrophysiology vol. 19, Nov. 1996, Part II, pp. 1748-1757.

Yu, et al., "Does Biventricular Pacing Provide Better Cardiac Function Than Univentricular Pacing In Normal Dogs?", Abstract, Heart Failure Society Abstracts-on-Disk, Sep. 13-16, 1998, Boca Raton, Florida, one page.

Auricchio, A., et al., "Acute Pacing Of The Left Ventricle Is Associated With Largest Hemodynamic Improvements in PTH-CHF Heart Failure Patients", Abstract, Heart Failure Society Abstracts-on-Disk, Sep. 13-16, 1998, Boca Raton, Florida, one page.

Leclercq, C., et al., "Comparative Effects of Permanent Biventricular Pacing In Class III and Class IV Patients", Pacing and Clincial Eelctrophysiology, Apr. 1998, vol. 21, No. 4, Part II, p. 911.

Bakker, P.F., et al., "Beneficial Effects Of Biventricular Pacing of Congestive Heart Failure" PACE, vol. 17, Apr. 1994, Part II, one page.

Bakker, P.F., et al. Biventricular Pacing Improves Functional Capacity In Patients With End-Stage Congestive Heart Failure, PACE, Apr. 1995, Part II, one page.

"The Latest Tetralogy of Fallot Discussion With Graphical Support Including Video Of Echocardiography And Catheterization", Pediatric ElectrophysiologyplcuBOOK ("An On-Line Resource For Pediatric Critical Care") (web address: http://pedsccm.wustl.edu/all-net/english/cardpage/electrlc/vcsurg/dysrh-8.htm.).

Zipes, D., et al., Cardiac Electrophysiology From Cell To Bedside, 1990, W.B. Saunders Co., Philadelphia 1990, Chapters 2, 6, 8, 10, 22, 87, 99-102, and 104.

Josephson, M.E., Clinical Cardiac Electrophysiology: Techniques And Interpretations, 2nd Edition, Lea & Febiger, Philadelphia, 1991, Chapter 13, pp. 658-709.

* cited by examiner

EXCITABLE TISSUE CONTROL SIGNAL DELIVERY TO THE RIGHT VENTRICULAR SEPTUM

CROSS-REFERENCE TO RELATED APPLICATIONS

This application is a continuation of co-pending, commonly assigned U.S. patent application Ser. No. 09/848,535, filed May 3, 2001, which is based upon commonly assigned U.S. Provisional Patent Application Ser. No. 60/202,382, filed May 14, 2000; a continuation-in-part of commonly assigned U.S. patent application Ser. No. 10/188,726, filed Jul. 2, 2002, which is a continuation of commonly assigned U.S. patent application Ser. No. 09/254,903, filed Mar. 12, 1999, now U.S. Pat. No. 6,415,178, which is a U.S. National Phase Patent Application of PCT Patent Application No. PCT/IL97/00233, filed Jul. 9, 1997, which is based upon U.S. Provisional Patent Application Ser. No. 60/026,392, filed Sep. 16, 1996, and Israeli Patent Application No. 119,261, filed Sep. 17, 1996; and a continuation-in-part of commonly assigned U.S. patent application Ser. No. 10/039,845, filed Oct. 23, 2001, which is a continuation of U.S. patent application Ser. No. 09/563,544, filed May 1, 2000, now U.S. Pat. No. 6,363,279, which is a continuation of U.S. patent application Ser. No. 09/101,723, filed Aug. 13, 1998, now U.S. Pat. No. 6,317,631 which is a U.S. National Phase filing of PCT Patent Application No. PCT/IL97/00012, filed Jan. 8, 1997, which is based upon U.S. Provisional Patent Application Ser. No. 60/009,769, filed Jan. 11, 1996, U.S. Provisional Patent Application Ser. No. 60/011,117, filed Feb. 5, 1996, U.S. Provisional Patent Application Ser. No. 60/026,392, filed Sep. 16, 1996, U.S. patent application Ser. No. 08/595,365, filed Feb. 1, 1996, now U.S. Pat. No. 5,738,096, and Israeli Patent Application No. 119,261, filed Sep. 17, 1996, each of which is incorporated herein in its entirety.

FIELD OF THE INVENTION

The present invention relates generally to invasive devices and methods for treatment of the heart, and specifically to devices and methods for improving cardiac performance.

BACKGROUND OF THE INVENTION

The heart requires precise coordination of its mechanical and electrical behavior to function optimally. The human body normally regulates cardiac output in response to body needs by changing the heart rate, as during physical exercise, and/or by adapting the stroke volume. Under pathological conditions, however, some of the normal regulatory mechanisms may be damaged. For example, heart tissue damaged due to myocardial infarct typically cannot sustain normal pumping function. Alternatively or additionally, normal electrical signals are not generated, or are impaired in their propagation, such that cardiac output and cardiac efficiency (stroke work divided by oxygen consumption) are correspondingly compromised. Standard pacemakers known in the art are able to control the rate of the heart, e.g., to accelerate the heart rate after detecting bradycardia, but are not able to increase contraction strength over the long-term without producing adverse side-effects.

PCT Patent Publication WO 97/25098, to Ben-Haim et al., entitled "Electrical muscle controller," and the corresponding U.S. patent application Ser. No. 09/101,723, which are assigned to the assignee of the present patent application and are incorporated herein by reference, describe methods for modifying the force of contraction of at least a portion of a heart chamber by applying a non-excitatory electric signal to the heart at a delay after electrical activation of the portion. The non-excitatory signal is such as does not induce action potentials in cardiac muscle cells, but rather modifies the cells' response to the activation. In the context of the present patent application, the use of such a non-excitatory signal is referred to as Excitable-Tissue Control (ETC). The non-excitatory signal may be applied in combination with a pacemaker or defibrillator, which applies an excitatory signal (i.e., pacing or defibrillation pulses) to the heart muscle.

PCT Patent Publication WO 98/10832, to Ben-Haim et al., entitled "Cardiac output enhanced pacemaker," and the corresponding U.S. patent application Ser. No. 09/254,900, which are assigned to the assignee of the present patent application and incorporated herein by reference, describe a pacemaker that gives cardiac output enhancement. This pacemaker applies both excitatory (pacing) and non-excitatory (ETC) electrical stimulation pulses to the heart. By applying non-excitatory pulses of suitable strength, appropriately timed with respect to the heart's electrical activation, the contraction of selected segments of the heart muscle can be increased or decreased, thus increasing or decreasing the stroke volume of the heart.

SUMMARY OF THE INVENTION

It is an object of some aspects of the present invention to provide improved methods and apparatus for stimulating cardiac tissue.

It is a further object of some aspects of the present invention to provide improved methods and apparatus for enhancing cardiac performance.

It is still a further object of some aspects of the present invention to provide improved methods and apparatus for increasing cardiac output.

In preferred embodiments of the present invention, an electrical cardiac stimulator for improving the performance of the heart of a human subject applies an Excitable-Tissue Control (ETC) signal to the interventricular septum via one or more electrodes passed by catheter into the right ventricle. Preferably, but not necessarily, at least one electrode is screwed or otherwise fixed to the septum, and delivers the ETC signal during a refractory period of excitable tissue of the septum, so as to modify a characteristic of the mechanical behavior thereof.

It is noted that these embodiments of the present invention simplify the procedure of applying electrical signals to modulate cardiac contraction. It is known in the art to apply pacing signals to the left ventricle by the difficult procedure of passing a catheter through the coronary veins. It is also known in the art to make an incision in a patient's chest so as to implant pacing electrodes on the heart. It is further known in the art to pace both ventricles via an electrode placed on the interventricular septum, whereby pacing pulses generated by the electrode cause an activation wave to propagate through the septum, through normal conduction pathways of the heart. These prior art techniques differ from preferred embodiments of the present invention in that the prior art is directed towards stimulating one or both ventricles to contract, while these embodiments of the present invention provide means for modulating the mechanical behavior of the septum itself, substantially without inducing new action potentials.

Typically, each electrode conveys a particular waveform to the septum, which may differ in certain aspects from the waveforms applied to other electrodes. The particular waveform to be applied to each electrode is preferably determined by a control unit, initially under the control of a physician during a calibration period of the unit. Further preferably, the cardiac stimulator (or elements thereof) is implanted in the patient in a manner similar to that used to implant pacemakers or defibrillators known in the art. After the initial calibration period, the unit is generally able to automatically modify the waveforms as needed to maintain a desired level of performance of the stimulator. In many applications, standard pacing, cardioversion, and/or defibrillation capabilities are additionally incorporated into the stimulator.

In a preferred embodiment, one or more mechanical sensors, e.g., force transducers, strain gauges, pressure gauges, and/or motion sensors, are positioned in a vicinity of the heart, and are coupled to send mechanical-sensor signals to the control unit indicative of aspects of the heart's functioning. Alternatively or additionally, one or more physiological sensors, e.g., for measuring mixed venous oxygen saturation (SvO2) or thoracic electrical impedance, send physiological-sensor signals to the control unit. The various sensor signals serve as feedback to enable the control unit to iteratively adjust the ETC signal applied to the septum, so as to cause the sensor signals to converge to desired values. Alternatively or additionally, other sensors, such as sensing electrodes, blood pressure sensors, or flow transducers, are coupled to the heart or elsewhere on the patient's body, and send signals to the control unit which are used in determining modifications to parameters of the energy applied to the heart.

Further alternatively or additionally, the control unit analyzes the sensor signals to detect an onset of arrhythmia, for example, an ectopic heartbeat. In this case, the control unit preferably modifies or terminates application of the ETC signal responsive to the detection.

There is therefore provided, in accordance with a preferred embodiment of the present invention, a method for applying a signal to a heart of a human subject, including applying an Excitable-Tissue Control (ETC) signal to a site on the right ventricular septum of the heart.

Typically, applying the ETC signal includes configuring the signal to be capable of modifying contractility of a portion of the heart. For example, configuring the ETC signal may include configuring the signal to be capable of modifying contractility of the left ventricle of the heart, the septum, or the right ventricle of the heart.

Preferably, configuring the ETC signal includes configuring the signal to be capable of increasing contractility of the portion of the heart. Alternatively, configuring the ETC signal includes configuring the signal to be capable of decreasing contractility of the portion of the heart. In a preferred embodiment, configuring the ETC signal to be capable of decreasing the contractility includes configuring the signal to be capable of decreasing contractility of the septum.

For some applications, applying the ETC signal includes applying a series of biphasic pulses. Alternatively or additionally, applying the ETC signal includes applying a series of generally square pulses. Further alternatively or additionally, applying the ETC signal includes applying a series of pulses at a rate greater than about 50 Hz. Still further alternatively or additionally, applying the ETC signal includes applying a series of pulses at a rate less than about 100 Hz.

Preferably, applying the ETC signal includes applying a series of pulses which are greater than about 8 mA. For some applications, applying the ETC signal includes applying a series of pulses which are greater than about 10 mA.

In a preferred embodiment of the present invention, applying the ETC signal includes applying the ETC signal to a site at or adjacent to an intersection of the septum and the right ventricular free wall.

There is also provided, in accordance with a preferred embodiment of the present invention, apparatus for applying a signal to a heart of a human subject, including:

a set of one or more electrodes, adapted to be coupled to the right ventricular septum of the heart; and a control unit, adapted to drive the electrode set to apply an Excitable-Tissue Control (ETC) signal to the septum.

The present invention will be more fully understood from the following detailed description of the preferred embodiments thereof, taken together with the drawings, in which:

DETAILED DESCRIPTION OF PREFERRED EMBODIMENTS

Figure 1A:
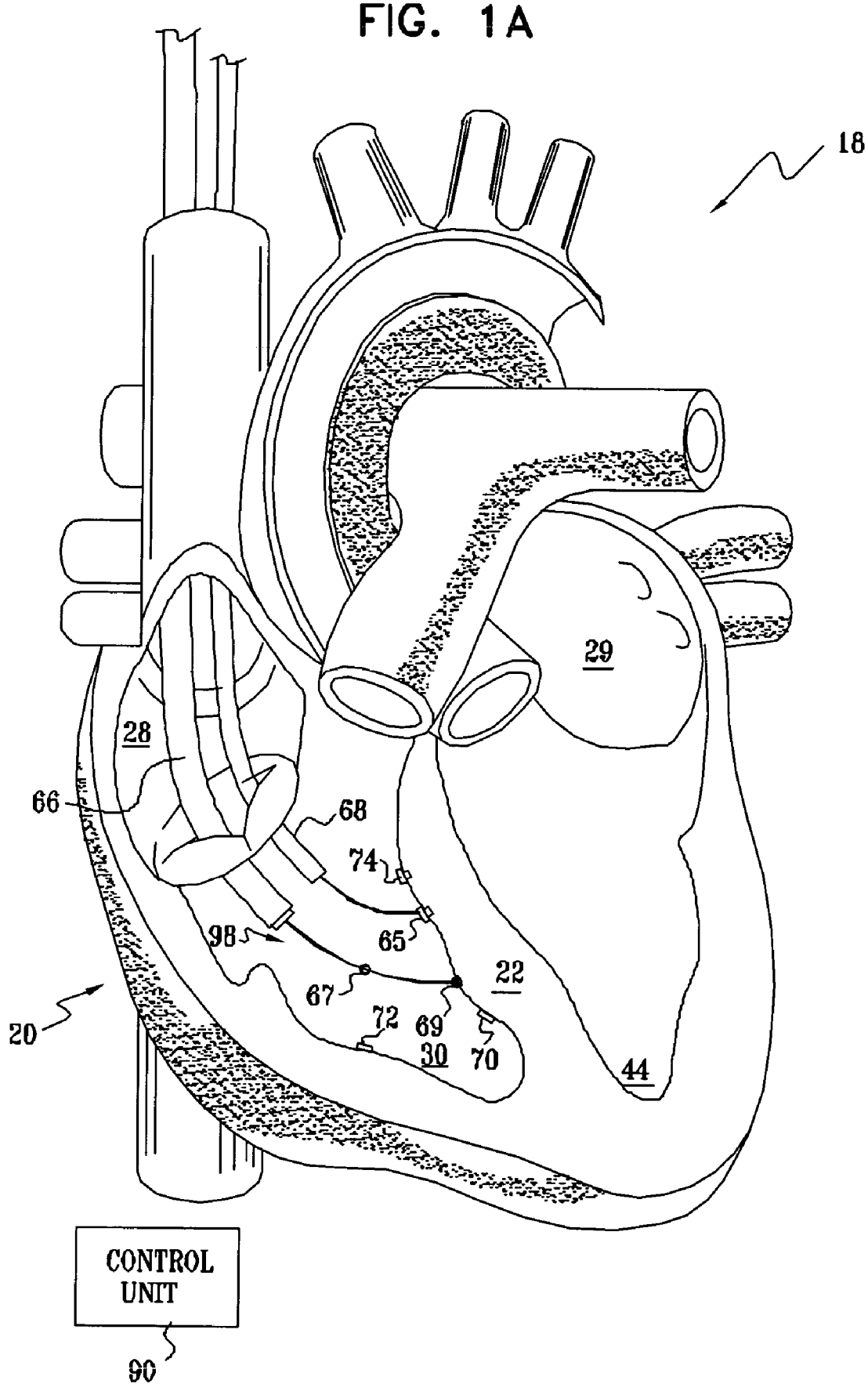
FIGS. 1A, 1B, and 1C are schematic, sectional illustrations of a heart, showing the placement of electrodes therein, in accordance with preferred embodiments of the present invention.

FIG. 1A is a schematic illustration of cardiac control apparatus 18, which applies electrical energy to improve the performance of the heart 20 of a patient, in accordance with a preferred embodiment of the present invention. Apparatus 18 preferably comprises an implantable or external control unit 90, which applies an ETC signal through a set of one or more electrodes 98 to the heart. (For clarity, connections between control unit 90 and the various electrodes are not shown.)

Preferably, a catheter 68 is used to convey a screw electrode 65, or other type of electrode, through the right ventricle 30 to a site on the interventricular septum 22 to which the electrode is attached. Alternatively or additionally, a catheter 66 conveys an electrode 69 through the right ventricle to be fixed to the septum, and/or conveys an electrode 67 into the right ventricle, where it is in electrical contact with electrodes 65 and 69 through the blood in the right ventricle. In a preferred embodiment, one or more electrodes are placed at or adjacent to the intersection of the septum and the right ventricular free wall.

Preferably, at least some of the electrodes have a coating applied thereto which increases the electrodes' capacitance. A preferred coating comprises iridium oxide (IROX). Alternatively or additionally, at least some of the electrodes comprise coils, a mesh, or other means for increasing the effective application area of the ETC signal.

As described hereinbelow, control unit 90 drives one or more of the electrodes to apply an ETC signal to the septum, so as to modify an aspect of the heart's contractility. For example, the signal may be applied so as to increase or decrease contractility of the right ventricle, the left ventricle, or the septum. Optionally, the control unit is implanted in the patient's body, and a metal case of the control unit serves as a return electrode for current driven through the electrodes in right ventricle 30.

Preferably, aspects of ETC signal application are performed in accordance with techniques described in the above-referenced U.S. patent application Ser. Nos. 09/101,723 and 09/254,900. Typically, the ETC signal is applied subsequent to an artificial pacing pulse, as described hereinbelow. Alternatively, the ETC signal is applied responsive to natural electrical activity of the heart, for example, after a designated delay following a detected activation of the atrium. For these applications, it is preferable to use apparatus and methods described in Israel Patent Application 129,257, entitled "Trigger-based regulation of excitable tissue control in the heart," which is assigned to the assignee of the present invention and is incorporated herein by reference.

Control unit 90 is optionally coupled to one or more local sense electrodes 74, which are placed in the right ventricle or elsewhere on or in the heart. Local sense electrodes 74 preferably convey electrical signals to the control unit responsive to cardiac electric activity. Alternatively or additionally, one or more of electrodes 98 and any other electrodes coupled to control unit 90 may also serve as sense electrodes. Optionally, one or more mechanical sensors 70 (e.g., accelerometers, force transducers, strain gauges, or pressure gauges), coupled to the control unit, are placed on the right ventricle or elsewhere on the heart. Alternatively or additionally, one or more supplemental sensors 72 (e.g., blood pressure, thoracic electrical impedance, pH, SvO2, pCO2 or pO2 sensors) are coupled to the control unit and are placed on or in the heart or elsewhere on or in the patient's body. The control unit modifies the energy applied through electrodes 98 responsive to signals from sensors 70 and 72 and local sense electrodes 74, as described hereinbelow.

The number of electrodes and sensors, as well as the positions thereof, are shown in FIG. 1A by way of example, and other sites on heart 20 or in a vicinity thereof are appropriate for placement of some of the electrodes and sensors in other applications of the present invention.

Preferably, control unit 90 is implanted in the patient in a manner similar to that used to implant pacemakers or defibrillators known in the art, such that after an initial calibration period, described hereinbelow, the unit is generally able to automatically modify the ETC signal it applies to the heart as needed, so as to maintain a desired level of performance. In many applications, standard pacing, cardioversion, and defibrillation capabilities are additionally incorporated into apparatus 18.

Figure 1B:
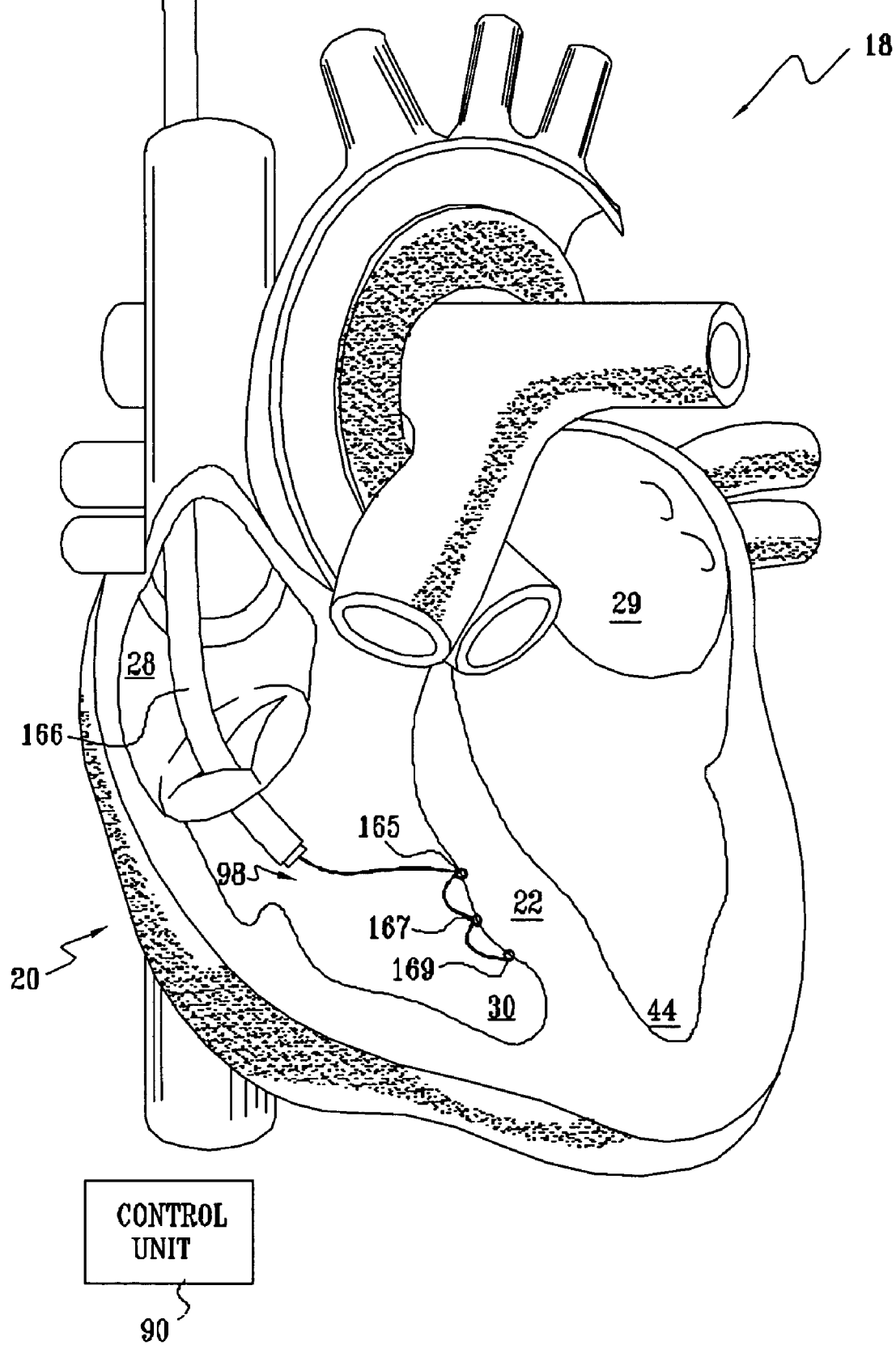
Figure 1C:
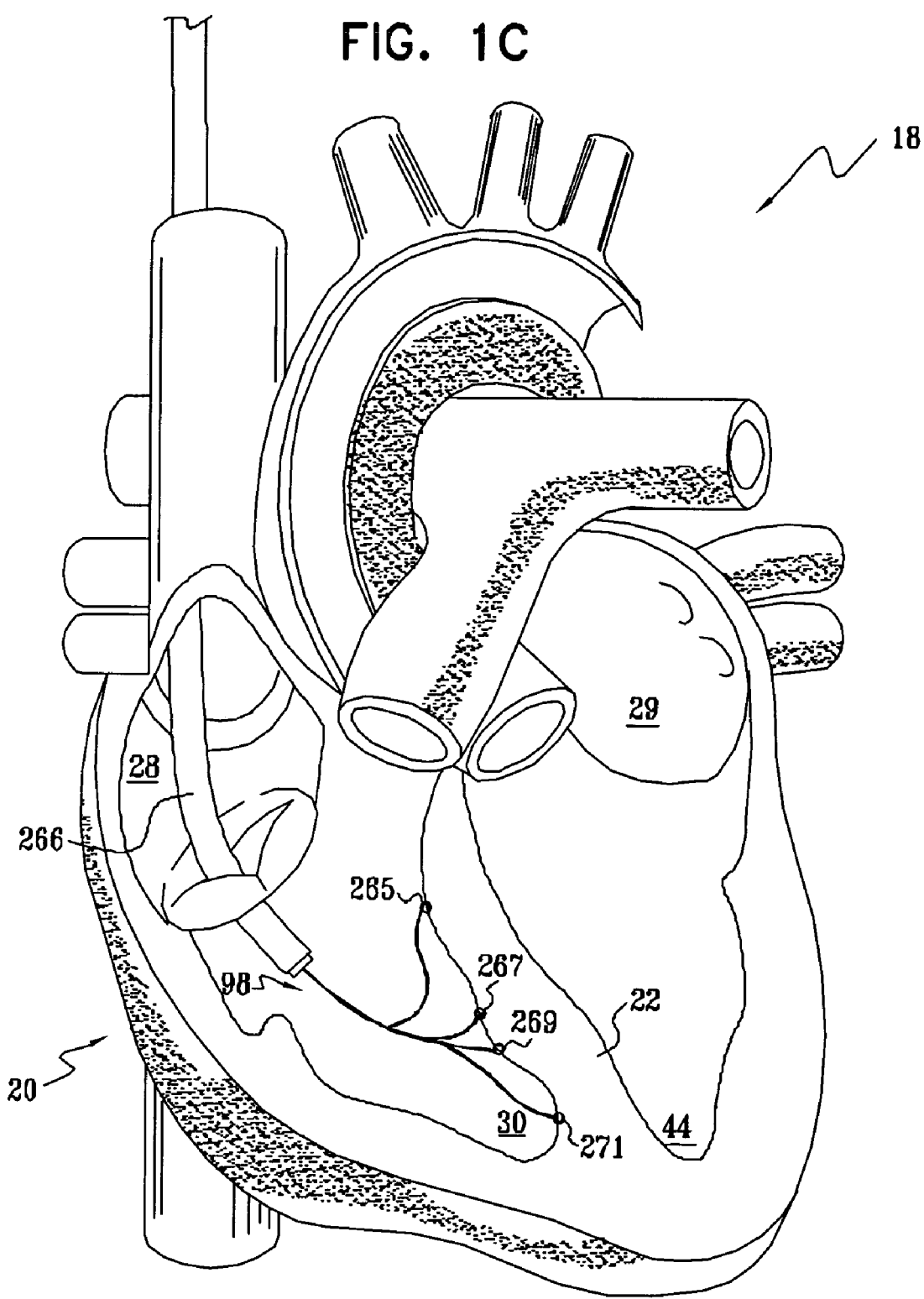

FIGS. 1B and 1C are schematic illustrations of other preferred configurations of cardiac control apparatus 18, in accordance with respective preferred embodiments of the present invention. FIG. 1B shows a catheter 166, which conveys a plurality of electrodes 165, 167, and 169 to respective sites on the right ventricular septum, while FIG. 1C shows a catheter 266, which conveys a different arrangement of electrodes 265, 267, 269, and 271 to the septum. In another preferred embodiment (not shown), a catheter passes a basket electrode into the right ventricle, so as to apply the ETC signal to the septum as well as to other right ventricular sites. Preferably, but not necessarily, all of the electrodes shown in FIGs. 1A, 1B, and 1C are independently controlled by control unit 90.

Figure 2:
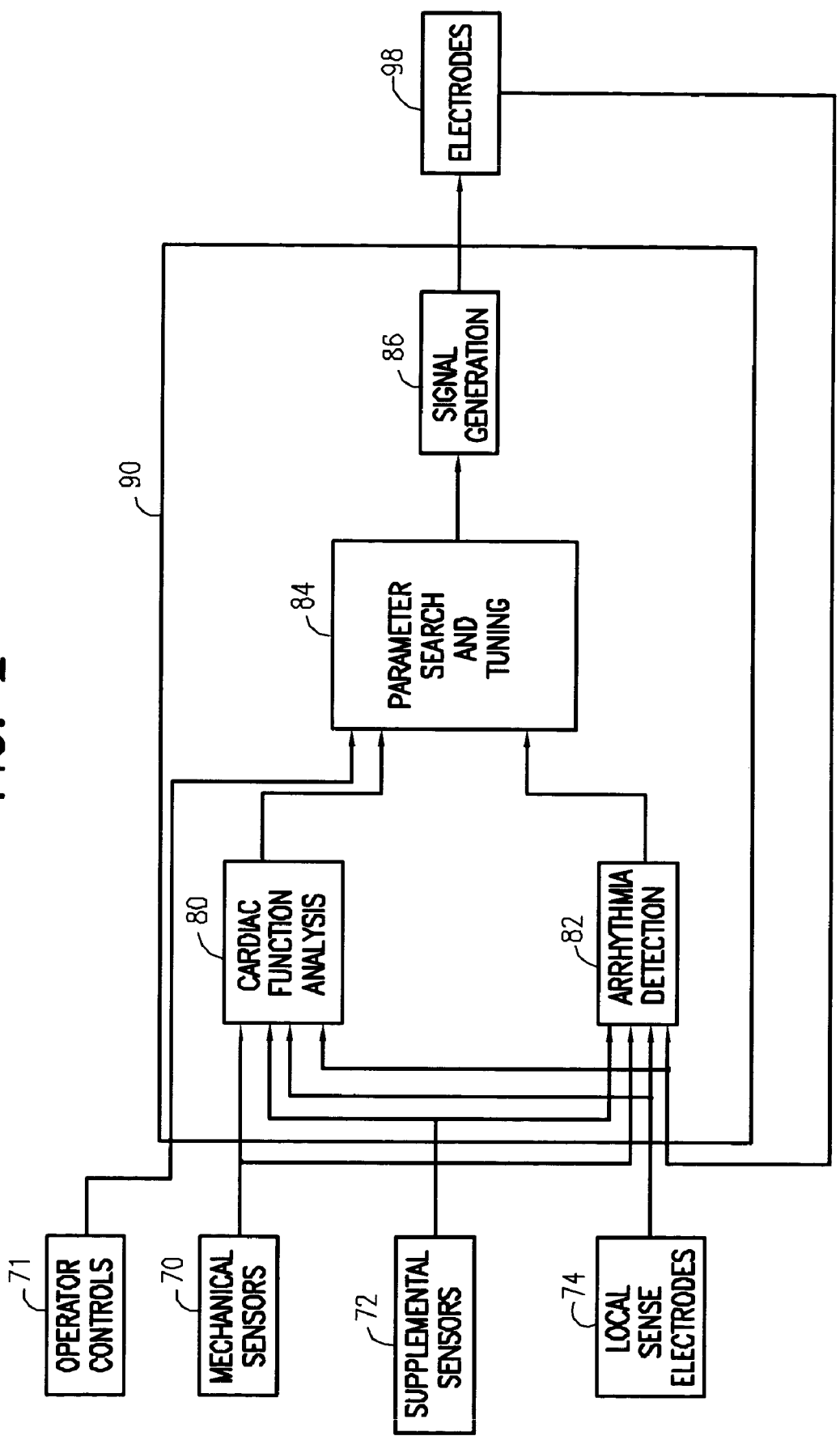
FIG. 2 is a schematic block diagram of a control unit, which generates signals to be applied to the electrodes shown in FIGS. 1A, 1B, and/or 1C, in accordance with a preferred embodiment of the present invention.

FIG. 2 is a schematic block diagram of control unit 90, in accordance with a preferred embodiment of the present invention. Mechanical sensors 70, supplemental sensors 72, local sense electrodes 74, and electrodes 98 are preferably coupled to provide feedback signals to a cardiac function analysis block 80 of control unit 90. The feedback signals generally provide information about various aspects of the heart's performance to block 80, which analyzes the signals and actuates control unit 90 to modify the electrical energy applied to the heart responsive to the analysis. Preferably, the ETC signal is adjusted by the control unit responsive to the feedback signals in order to yield a desired response, e.g., a predetermined blood pressure, blood oxygen level, cardiac output and/or cardiac electrical or motion profile.

Preferably, block 80 conveys results of its analysis to a "parameter search and tuning" block 84 of control unit 90, which iteratively modifies characteristics of the electrical energy applied to the heart in order to attain a desired response. Preferably, operating parameters of block 84 are entered by a human operator of the control unit using operator controls 71, which typically comprise a keyboard or mouse (not shown) coupled to the control unit. Block 84 typically utilizes multivariate optimization and control methods known in the art in order to cause one or more of the aforementioned mechanical, electrical, chemical and/or other measured parameters to converge to desired values.

In general, each one of electrodes 98 may convey a particular waveform to heart 20, differing in certain aspects from the waveforms applied by the other electrodes. The particular waveform to be applied by each electrode is determined by control unit 90, preferably under the control of the operator. Aspects of the waveforms which are set by the control unit, and may differ from electrode to electrode, typically include parameters such as time shifts between application of waveforms at different electrodes, waveform shapes, amplitudes, DC offsets, durations, and duty cycles. For example, although the waveforms applied to some or all of electrodes 98 usually comprise a biphasic square wave signal following a natural or applied pacing pulse, other waveforms, such as a sinusoid, a series of monophasic square waves, or a waveform including an exponentially-varying characteristic, could be applied to other electrodes. Generally, the shape, magnitude, and timing of the waveforms are optimized for each patient, using suitable optimization algorithms as are known in the art.

For the purposes of this embodiment of the present invention, block 84 typically modifies a set of controllable parameters of the ETC signal, responsive to the measured parameters, in accordance with values in a look-up table and/or pre-programmed formulae stored in an electronic memory of control unit 90. The controllable parameters may comprise, for example, ETC signal timing, magnitude and offset. Preferably, the controllable parameters are conveyed by block 84 to a signal generation block 86 of control unit 90, which generates, responsive to the parameters, electrical signals that are applied by electrodes 98 to the heart. Block 86 preferably comprises amplifiers, isolation units, and other standard circuitry known in the art of electrical signal generation.

In the initial calibration procedure, parameter search and tuning block 84 preferably modifies a characteristic (e.g., timing, magnitude, or shape) of the ETC signal applied through one of electrodes 98, and then determines whether a predetermined cardiac functional response generally improves following the modification. For example, the electrode may be used to sense the duration of the refractory period of heart tissue to which the electrode is coupled, and block 84 may subsequently determine time points during the refractory period which are optimal for application of the ETC signal by that electrode to the tissue. In a series of similar calibration steps, block 84 repeatedly modifies characteristics of the energy applied through each of the electrodes, such that those modifications that improve the response are generally maintained, and modifications that cause it to worsen are typically eliminated or avoided.

When apparatus 18 is calibrated in the presence of a physician, it is often desirable to have the patient perform increasing levels of exercise (e.g., walk on a treadmill), in order to derive a broader range of operating parameters, which are stored in control unit 90 and can be accessed responsive to signals from the sensors and electrodes coupled to the control unit. Preferably, the calibration procedure is subsequently performed by the physician at intermittent follow-up visits, and/or by unit 90 automatically during regular use of the apparatus (e.g., daily).

Preferably, during the initial calibration procedure, the locations of one or more of electrodes 98 are varied while the ETC signal is applied therethrough, so as to determine optimum placement of the electrodes. Preferably, methods for measuring the heart's response to the applied signal include electrocardiography, echocardiography, and/or methods having as inputs the outputs of mechanical and supplemental sensors 70 and 72. In subsequent steps, the electrode is moved over an area of the interventricular septum, and the response of the heart is measured. After the physician considers that a sufficient number of sites have been investigated, the electrode is returned to the site yielding the best response. Subsequently, other electrodes are moved according to the same protocol, so as to achieve substantially optimum placement of some or all of the electrodes.

In a preferred embodiment, the ETC signal is applied in a vicinity of a site where standard pacing pulses are applied. Preferably, the ETC signal is applied through the same electrode as that through which the standard pacing pulse is applied, approximately 1–250 ms thereafter. Further preferably, the ETC signal is applied approximately 20–250 ms after the pacing pulse.

Alternatively, the sinoatrial node generates the cardiac rhythm, substantially without artificial pacing. In such modes, local sense electrodes 74 and, optionally, some or all of electrodes 98, convey electrical signals to control unit 90, so as to enable parameter search and tuning block 84 to synchronize the electrical signals applied by electrodes 98 with the natural electrical activity of the heart. It will be understood that although electrodes 74 and 98 are shown for clarity of explanation as separate entities, a single set of electrodes may be used to perform both functions.

In a preferred embodiment, the ETC signal is applied at one or more sites as a series of pulses, e.g., biphasic square pulses, typically having a frequency between about 50 and 100 Hz. The current applied during each pulse is preferably greater than 8 mA, and, further preferably, greater than 10 mA.

Most preferably, during calibration and during regular operation of control unit 90, an arrhythmia detection block 82 of control unit 90 receives inputs from sensors 70 and 72 and electrodes 74 and 98, and/or other electrodes and sensors (not shown), and evaluates these inputs to detect imminent or actual cardiac arrhythmia, e.g., an ectopic heartbeat, fibrillation, bradycardia or heart block. Preferably, block 82 employs techniques known in the art for detecting arrhythmias, so that parameter search and tuning block 84 can treat or terminate the arrhythmia by applying, for example, regular pacing pulses or defibrillation pulses.

Figure 3:
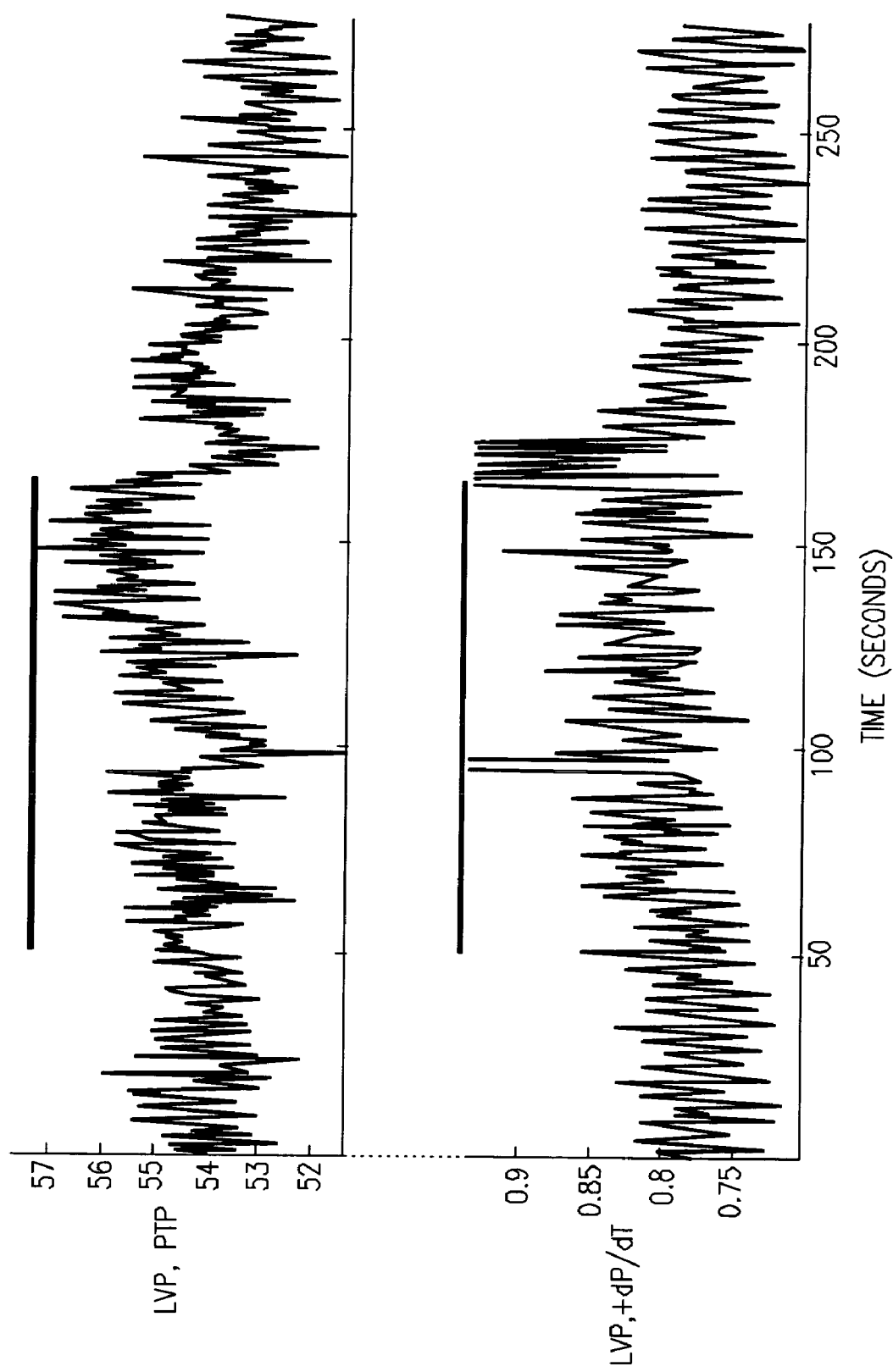
FIGS. 3, 4, and 5 are graphs showing experimental results from the application of an ETC signal to an animal heart, in accordance with a preferred embodiment of the present invention.
Figure 4:
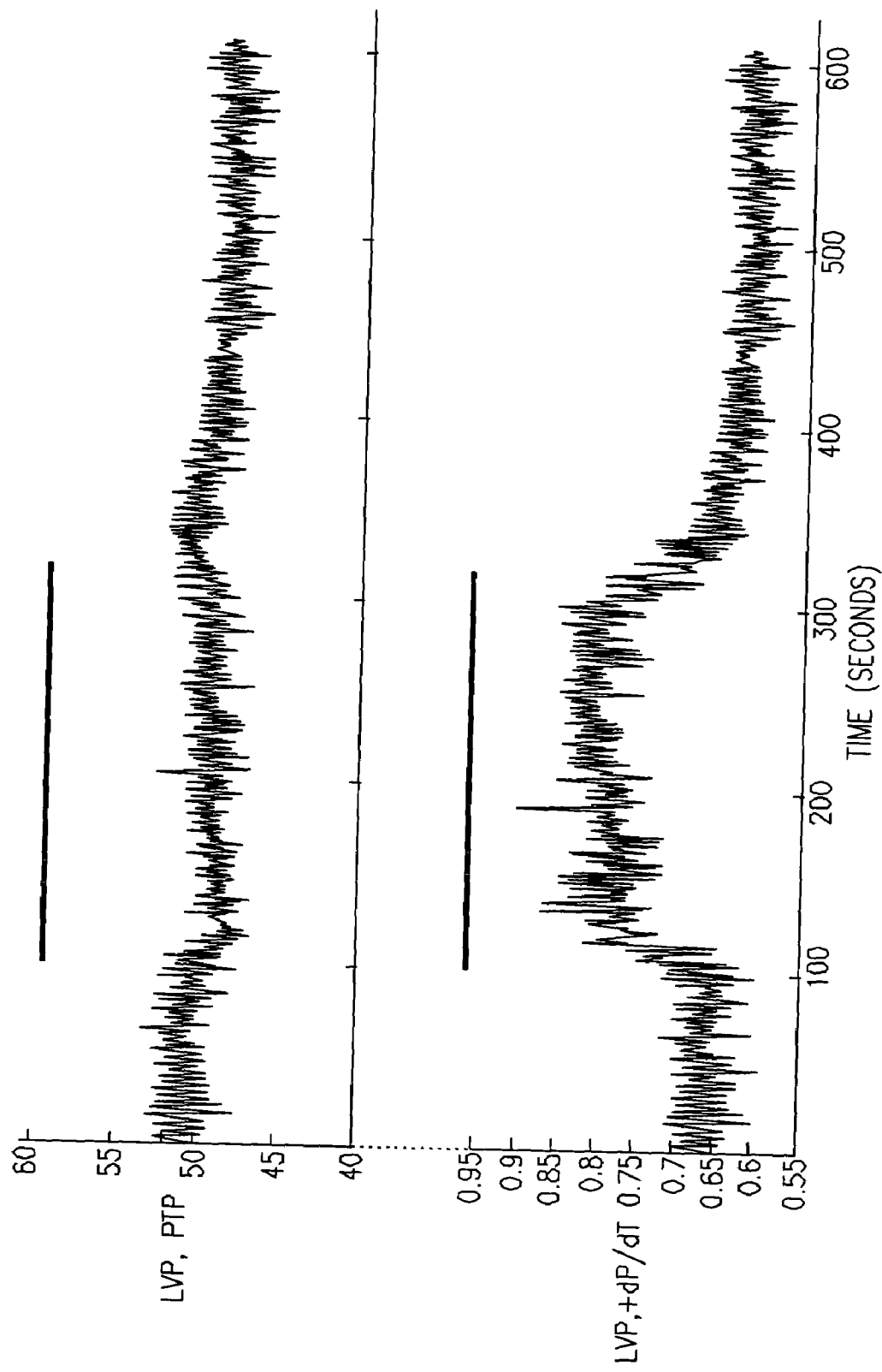
Figure 5:
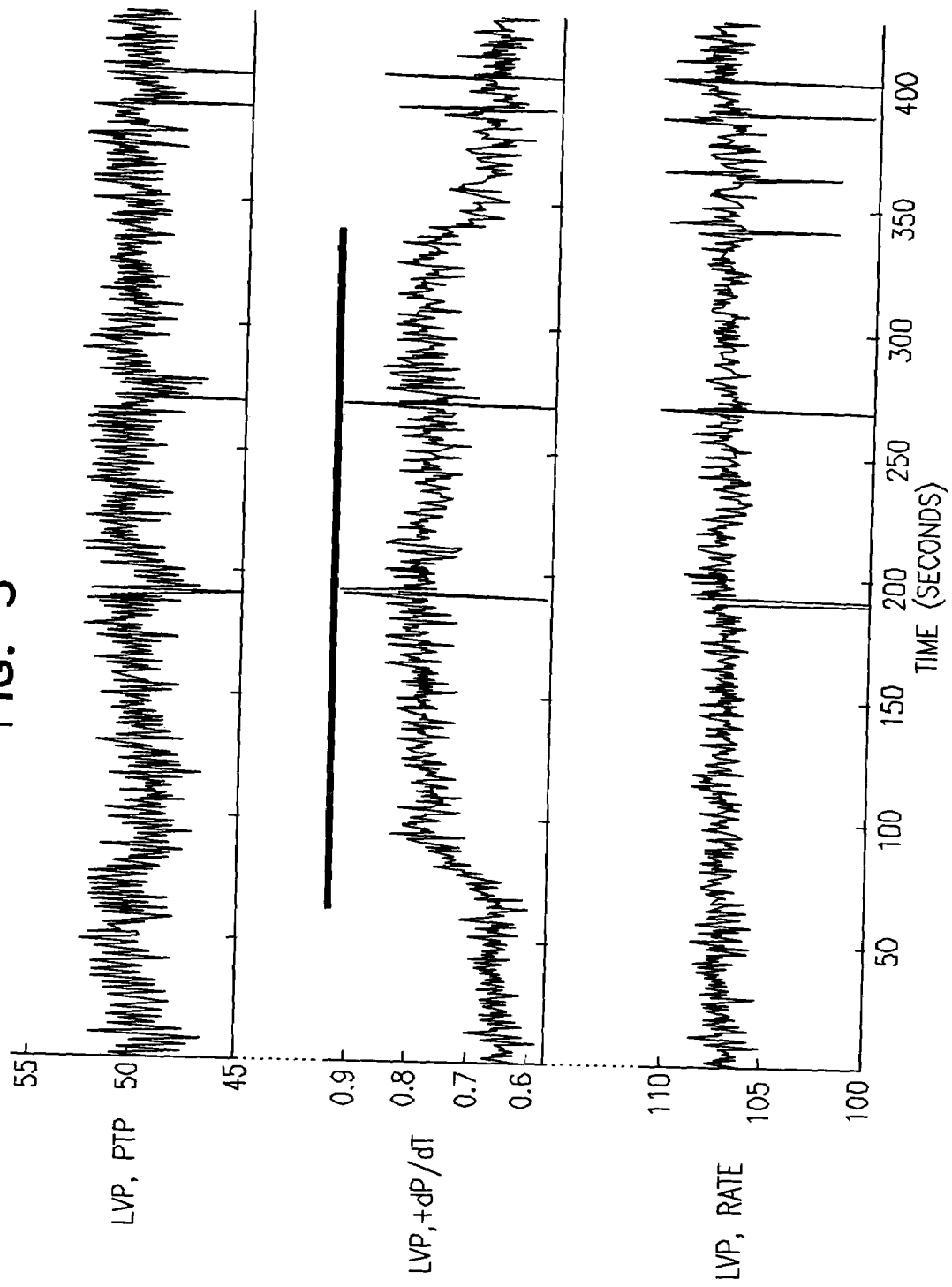

FIGS. 3, 4, and 5 are graphs showing experimental results obtained during application of an ETC signal to a 30 kg anesthetized pig, in accordance with a preferred embodiment of the present invention. In this experiment, local sense electrodes comprised two stitch electrodes, which were placed at the mid-anterior wall of the left ventricle. The animal was paced in DDD mode at 120 beats per minute through an active fixation screw electrode, placed in the apical third of the right ventricular septum. At 20 ms following the onset of electrical activity as measured by the local sense electrodes, a biphasic electrical signal, composed of a 15 ms, +14 mA pulse immediately followed by a 15 ms, −14 mA pulse, was applied to the septum through the screw electrode implanted therein. In FIG. 3, results are shown following application of the ETC signal between the screw electrode implanted in the septum and a ring electrode in a vicinity thereof. FIGS. 4 and 5 show results following application of the ETC signal between the screw electrode and a stitch electrode at the mid-anterior left ventricular free wall.

In FIG. 3, an increase of approximately 5% in the measured d(LVP)/dt is seen to begin upon initiation of a 2 minute ETC signal application period. The dP/dt levels gradually return to baseline upon termination of the ETC signal. FIGS. 4 and 5 show bipolar ETC application periods lasting over 3 and over 4 minutes, respectively, in which the measured dP/dt increased to approximately 20% above baseline, and remained at this level for the duration of signal application.

It is believed that at least some of the results displayed in FIGS. 3, 4, and 5 derive from a change in contractility of the left ventricle induced by the application of the ETC signal to the interventricular septum.

It is also believed that similar results can be obtained in humans, mutatis mutandis. It is further believed that these embodiments of the present invention can produce, at least to some extent, long-term effects which are likely to alleviate or cure aspects of some common cardiac pathologies such as congestive heart failure (CHF). These effects are expected to derive from more effective use of the heart muscle, whereby systemic demands on the heart are reduced. Moreover, damage to other organs of the body is reduced, because of the increase in blood perfusion.

It is believed that other signal application protocols would also be successful in enhancing cardiac performance, in combination with or in the absence of some of the stimulation and sensing protocols described hereinabove. In a preferred embodiment, the ETC signal is applied at a plurality of sites on the interventricular septum, for example, on an anterior and a posterior aspect thereof. Alternatively or additionally, the ETC signal is applied generally simultaneously, or in alternation, at one or more of the following sites: the posterior septum, the anterior septum, the anterior wall of the right ventricle, the free wall of the right ventricle, and the posterior-inferior left ventricular free wall.

Alternatively or additionally, the ETC signal is applied through the right ventricular septum so as to decrease regional contractility of the heart, preferably using techniques described in one or both of the above-referenced US patent applications. In particular, the ETC signal may be used to decrease septal contractility, which may be appropriate in treating conditions such as idiopathic hypertrophic subaortic stenosis (IHSS). It is believed that reduced septal contractility reduces functional subaortic stenosis, thereby improving left ventricular performance.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

The invention claimed is:

1. A method for applying a signal to a heart of a human subject, comprising applying an Excitable-Tissue Control (ETC) signal to a site on the right ventricular septum of the heart.

2. A method according to claim 1, wherein applying the ETC signal comprises configuring the signal to be capable of modifying contractility of a portion of the heart.

3. A method according to claim 2, wherein configuring the ETC signal comprises configuring the signal to be capable of modifying contractility of the left ventricle of the heart.

4. A method according to claim 2, wherein configuring the ETC signal comprises configuring the signal to be capable of modifying contractility of the septum.

5. A method according to claim 2, wherein configuring the ETC signal comprises configuring the signal to be capable of modifying contractility of the right ventricle of the heart.

6. A method according to claim 2, wherein configuring the ETC signal comprises configuring the signal to be capable of increasing contractility of the portion of the heart.

7. A method according to claim 2, wherein configuring the ETC signal comprises configuring the signal to be capable of decreasing contractility of the portion of the heart.

8. A method according to claim 7, wherein configuring the ETC signal to be capable of decreasing the contractility comprises configuring the signal to be capable of decreasing contractility of the septum.

9. A method according to claim 1, wherein applying the ETC signal comprises applying a series of biphasic pulses.

10. A method according to claim 1, wherein applying the ETC signal comprises applying a series of generally square pulses.

11. A method according to claim 1, wherein applying the ETC signal comprises applying a series of pulses at a rate greater than about 50 Hz.

12. A method according to claim 1, wherein applying the ETC signal comprises applying a series of pulses at a rate less than about 100 Hz.

13. A method according to claim 1, wherein applying the ETC signal comprises applying a series of pulses at a rate between about 50 Hz and 100 Hz.

14. A method according to claim 1, wherein applying the ETC signal comprises applying a series of pulses which are greater than about 8 mA.

15. A method according to claim 14, wherein applying the ETC signal comprises applying a series of pulses which are greater than about 10 mA.

16. A method according to claim 1, wherein applying the ETC signal comprises applying the ETC signal to a site at or adjacent to an intersection of the septum and the right ventricular free wall.

17. Apparatus for applying a signal to a heart of a human subject, comprising:
    a set of one or more electrodes, adapted to be coupled to the right ventricular septum of the heart; and
    a control unit, adapted to drive the electrode set to apply an Excitable-Tissue Control (ETC) signal to the septum.

18. Apparatus according to claim 17, wherein the control unit is adapted to configure the signal to be capable of modifying contractility of a portion of the heart.

19. Apparatus according to claim 18, wherein the control unit is adapted to configure the signal to be capable of modifying contractility of the left ventricle of the heart.

20. Apparatus according to claim 18, the control unit is adapted to configure the signal to be capable of modifying contractility of the septum.

21. Apparatus according to claim 18, wherein the control unit is adapted to configure the signal to be capable of modifying contractility of the right ventricle of the heart.

22. Apparatus according to claim 18, wherein the control unit is adapted to configure the signal to be capable of increasing contractility of the portion of the heart.

23. Apparatus according to claim 18, wherein the control unit is adapted to configure the signal to be capable of decreasing contractility of the portion of the heart.

24. Apparatus according to claim 23, wherein the control unit is adapted to configure the signal to be capable of decreasing contractility of the septum.

25. Apparatus according to claim 17, wherein the control unit is adapted to drive the electrode set to apply a series of biphasic pulses.

26. Apparatus according to claim 17, wherein the control unit is adapted to drive the electrode set to apply a series of generally square pulses.

27. Apparatus according to claim 17, wherein the control unit is adapted to drive the electrode set to apply a series of pulses at a rate greater than about 50 Hz.

28. Apparatus according to claim 17, wherein the control unit is adapted to drive the electrode set to apply a series of pulses at a rate less than about 100 Hz.

29. Apparatus according to claim 17, wherein the control unit is adapted to drive the electrode set to apply a series of pulses at a rate between about 50 Hz and 100 Hz.

30. Apparatus according to claim 17, wherein the control unit is adapted to drive the electrode set to apply a series of pulses which are greater than about 8 mA.

31. Apparatus according to claim 30, wherein the control unit is adapted to drive the electrode set to apply a series of pulses which are greater than about 10 mA.

32. Apparatus according to claim 17, wherein the control unit is adapted to drive the electrode set to apply the ETC signal to a site at or adjacent to an intersection of the septum and the right ventricular free wall.

* * * * *